United States Patent
Poran et al.

(10) Patent No.: US 9,962,557 B2
(45) Date of Patent: *May 8, 2018

(54) AESTHETIC TREATMENT DEVICE AND METHOD

(71) Applicant: S & Y ENTERPRISES LLC, West Orange, NJ (US)

(72) Inventors: Yehuda Poran, Hazor Haglilit (IL); Oren Aharon, Haifa (IL)

(73) Assignee: S & Y ENTERPRISES LLC, West Orange, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/155,777

(22) Filed: May 16, 2016

(65) Prior Publication Data

US 2016/0256707 A1    Sep. 8, 2016

Related U.S. Application Data

(60) Division of application No. 14/137,116, filed on Dec. 20, 2013, now Pat. No. 9,364,684, which is a
(Continued)

(30) Foreign Application Priority Data

Jun. 22, 2012  (EP) .................................... 12173261

(51) Int. Cl.
*A61B 18/18*     (2006.01)
*A61B 18/20*     (2006.01)
(Continued)

(52) U.S. Cl.
CPC ............ *A61N 5/0616* (2013.01); *A61B 18/18* (2013.01); *A61B 18/203* (2013.01);
(Continued)

(58) Field of Classification Search
None
See application file for complete search history.

(56) References Cited

U.S. PATENT DOCUMENTS

| 2,151,733 A | 3/1939 | Bonfield |
| 4,622,971 A | 11/1986 | Yamamoto ............... 219/121.61 |

(Continued)

FOREIGN PATENT DOCUMENTS

| DE | 2157990 | 11/1971 | |
| EP | 0913127 A2 * | 5/1999 | ........... A61B 18/203 |

(Continued)

OTHER PUBLICATIONS

International Search Report dated Oct. 28, 2013, issued to International Application No. PCT/US2013/043507.

(Continued)

*Primary Examiner* — Lynsey Eiseman
*Assistant Examiner* — Manolis Pahakis
(74) *Attorney, Agent, or Firm* — Stein IP, LLC

(57) ABSTRACT

An aesthetic treatment device including: a multi illumination system having at least one source in the visible region, disposed around a periphery of a predetermined area of skin; an imaging device, sensitive to the illumination system, to discern features on or in the skin within the predetermined area of skin to be treated; multiple treatment light sources mounted on an optical bench and aimed and focused to a point of treatment in the predetermined area of skin; a mechanical guidance system to guide the multiple treatment light sources; and a pulse generator to control power output of the multiple treatment light sources based upon the treatment to be applied to the predetermined area of skin.

9 Claims, 11 Drawing Sheets

Related U.S. Application Data continuation-in-part of application No. 13/903,129, filed on May 28, 2013, now Pat. No. 9,480,529.

(51) Int. Cl.
  *A61N 5/06* (2006.01)
  *A61B 17/00* (2006.01)
  *A61B 18/00* (2006.01)
  *A61N 5/067* (2006.01)

(52) U.S. Cl.
  CPC .. *A61N 5/0617* (2013.01); *A61B 2017/00057* (2013.01); *A61B 2018/00476* (2013.01); *A61B 2018/00642* (2013.01); *A61B 2018/00904* (2013.01); *A61B 2018/2065* (2013.01); *A61B 2018/20351* (2017.05); *A61N 2005/067* (2013.01); *A61N 2005/0626* (2013.01); *A61N 2005/0651* (2013.01); *A61N 2005/0662* (2013.01)

(56) References Cited

U.S. PATENT DOCUMENTS

| | | | |
|---|---|---|---|
| 4,905,690 A | 3/1990 | Ohshiro | 607/89 |
| 4,930,504 A | 6/1990 | Diamantopoulos | 250/494.1 |
| 5,054,502 A | 10/1991 | Courage | 600/587 |
| 5,102,409 A * | 4/1992 | Balgorod | A61F 9/00804 219/121.6 |
| 5,146,923 A | 9/1992 | Dhawan | 600/476 |
| 5,198,875 A | 3/1993 | Bazin et al. | 356/369 |
| 5,533,266 A * | 7/1996 | Kelman | A61B 18/203 132/200 |
| 5,807,387 A | 9/1998 | Druais | 219/121.78 |
| 5,820,625 A | 10/1998 | Izawa | 606/13 |
| 5,851,181 A * | 12/1998 | Talmor | A61B 5/0071 600/407 |
| 5,993,440 A * | 11/1999 | Ghassemi | B26B 19/00 30/41.5 |
| 6,019,482 A | 2/2000 | Everett | 362/184 |
| 6,032,071 A | 2/2000 | Binder | 600/476 |
| 6,063,108 A * | 5/2000 | Salansky | A61N 5/0616 606/13 |
| 6,070,092 A * | 5/2000 | Kazama | A61B 5/0059 600/310 |
| 6,081,612 A | 6/2000 | Gutkowicz-Krusin et al. | 382/128 |
| 6,210,425 B1 * | 4/2001 | Chen | A61N 5/062 600/436 |
| 6,251,102 B1 * | 6/2001 | Gruzdev | A61B 18/203 372/34 |
| 6,370,422 B1 | 4/2002 | Richards-Kortum | 600/182 |
| 6,413,267 B1 | 7/2002 | Dumoulin-White et al. | 607/89 |
| 6,702,837 B2 | 3/2004 | Gutwein | 606/9 |
| 6,736,807 B2 | 5/2004 | Yamazaki et al. | 606/9 |
| 6,790,205 B1 * | 9/2004 | Yamazaki | A61B 18/203 606/11 |
| 6,818,903 B2 | 11/2004 | Schomacker | 250/458.1 |
| 6,872,221 B2 | 3/2005 | Lytle | 128/898 |
| 7,006,223 B2 | 2/2006 | Mullani | 356/369 |
| 7,081,128 B2 * | 7/2006 | Hart | A61N 5/0616 607/88 |
| 7,214,222 B2 | 5/2007 | Yamazaki | 606/10 |
| 7,220,254 B2 | 5/2007 | Altshuler | 128/898 |
| 7,328,060 B2 | 2/2008 | Mooradian et al. | 600/476 |
| 7,369,692 B2 | 5/2008 | Shirai et al. | 382/128 |
| 8,475,506 B1 * | 7/2013 | Bendett | A61N 5/0622 607/88 |
| 8,496,695 B2 * | 7/2013 | Kang | A61B 5/0071 128/898 |
| 8,821,949 B2 | 9/2014 | Baszczok et al. | 601/15 |
| 9,622,818 B2 * | 4/2017 | Johnson | A61B 18/203 |
| 2002/0091322 A1 | 7/2002 | Chaiken | 600/476 |
| 2002/0173781 A1 | 11/2002 | Cense | 606/9 |
| 2002/0173782 A1 * | 11/2002 | Cense | A61B 18/203 606/9 |
| 2003/0026110 A1 | 2/2003 | Satoh et al. | 362/572 |
| 2003/0036751 A1 * | 2/2003 | Anderson | A61B 5/0059 606/9 |
| 2003/0045799 A1 | 3/2003 | Bazin | 600/476 |
| 2003/0050561 A1 | 3/2003 | Bazin | 600/476 |
| 2003/0055414 A1 * | 3/2003 | Altshuler | A61B 18/203 606/9 |
| 2003/0216716 A1 | 11/2003 | Desarzens | 606/10 |
| 2003/0216719 A1 | 11/2003 | Debenedictis | 606/10 |
| 2004/0006276 A1 * | 1/2004 | Demos | A61B 1/043 600/476 |
| 2004/0015156 A1 | 1/2004 | Vasily | 606/9 |
| 2004/0030370 A1 | 2/2004 | Lytle | 607/89 |
| 2004/0062056 A1 | 4/2004 | Heine | 362/555 |
| 2004/0082940 A1 | 4/2004 | Black | 606/9 |
| 2004/0174525 A1 | 9/2004 | Mullani | 356/369 |
| 2004/0210277 A1 | 10/2004 | Becker | 607/88 |
| 2004/0257439 A1 | 12/2004 | Shirai | 348/77 |
| 2004/0260209 A1 * | 12/2004 | Ella | A61B 18/203 601/7 |
| 2005/0020892 A1 | 1/2005 | Acosta | 600/316 |
| 2005/0045189 A1 * | 3/2005 | Jay | A61B 5/0059 128/898 |
| 2005/0049582 A1 * | 3/2005 | DeBenedictis | A61B 18/20 606/9 |
| 2005/0143719 A1 * | 6/2005 | Sink | A61B 18/203 606/9 |
| 2005/0154382 A1 | 7/2005 | Altshuler et al. | 606/9 |
| 2005/0177093 A1 * | 8/2005 | Barry | A61N 5/0616 604/20 |
| 2006/0009686 A1 | 1/2006 | Boukas | 600/315 |
| 2006/0095096 A1 | 5/2006 | DeBenedictis | 607/88 |
| 2006/0200116 A1 | 9/2006 | Ferren | 606/9 |
| 2006/0247741 A1 | 11/2006 | Hsu | 607/88 |
| 2006/0253176 A1 * | 11/2006 | Caruso | A61B 18/203 607/88 |
| 2007/0027411 A1 * | 2/2007 | Ella | A61H 7/008 601/7 |
| 2007/0049910 A1 * | 3/2007 | Altshuler | A61B 18/203 606/9 |
| 2007/0049996 A1 * | 3/2007 | Black | A61B 18/203 607/89 |
| 2007/0060819 A1 | 3/2007 | Altshuler et al. | 600/475 |
| 2007/0073156 A1 * | 3/2007 | Zilberman | A61B 5/0064 600/473 |
| 2007/0252997 A1 * | 11/2007 | Van Hal | A61B 5/0059 356/448 |
| 2008/0077198 A1 * | 3/2008 | Webb | A61N 5/0618 607/88 |
| 2008/0208104 A1 * | 8/2008 | Bragagna | A61B 18/203 604/20 |
| 2008/0287930 A1 * | 11/2008 | Rapoport | A61B 18/203 606/9 |
| 2008/0294151 A1 | 11/2008 | Whitaker et al. | 606/9 |
| 2009/0054880 A1 | 2/2009 | Aharon | 606/9 |
| 2009/0088824 A1 | 4/2009 | Baird | 607/90 |
| 2009/0099559 A1 | 4/2009 | Dhadwal | 606/9 |
| 2010/0049177 A1 | 2/2010 | Boone, III et al. | 606/9 |
| 2010/0063490 A1 * | 3/2010 | Verhagen | A61B 5/1077 606/9 |
| 2011/0013006 A1 * | 1/2011 | Uzenbajakava | A61B 5/0059 348/77 |
| 2011/0137303 A1 | 6/2011 | Dolleris et al. | 606/17 |
| 2011/0160712 A1 | 6/2011 | Tankovich | 606/9 |
| 2011/0313408 A1 * | 12/2011 | Tankovich | A61B 18/203 606/3 |
| 2012/0041283 A1 | 2/2012 | Krishnan | 600/306 |
| 2012/0226268 A1 * | 9/2012 | Liu | A61B 18/203 606/9 |
| 2012/0296322 A1 | 11/2012 | Yamazaki et al. | 606/9 |
| 2013/0018362 A1 * | 1/2013 | Verhagen | A61B 18/203 606/9 |
| 2013/0103017 A1 * | 4/2013 | Weckwerth | A61B 18/203 606/9 |

(56) References Cited

U.S. PATENT DOCUMENTS

| | | | | |
|---|---|---|---|---|
| 2014/0081148 A1* | 3/2014 | Heinrich | ................ | G01N 21/21 600/476 |
| 2014/0296837 A1* | 10/2014 | Varghese | ............... | A61B 5/448 606/9 |
| 2015/0080866 A1* | 3/2015 | Verhagen | ................ | B26B 19/38 606/9 |
| 2015/0202006 A1* | 7/2015 | Johnson | ............... | A61B 18/203 606/9 |
| 2015/0359592 A1* | 12/2015 | Moeskops | ............ | A61B 18/203 606/9 |

FOREIGN PATENT DOCUMENTS

| WO | WO 2005/065565 A1 | 7/2005 | | |
|---|---|---|---|---|
| WO | WO 2006/044652 A1 | 4/2006 | | |
| WO | WO 2008/124839 A1 | 10/2008 | | |
| WO | WO 2009/155501 A2 | 12/2009 | | |
| WO | WO 2011/116347 A1 | 9/2011 | | |
| WO | WO 2012/106678 A1 | 8/2012 | | |
| WO | WO 2013068932 A1 * | 5/2013 | ............. | A61B 5/448 |

OTHER PUBLICATIONS

U.S. Non-Final Office Action dated Sep. 16, 2015, issued to the corresponding U.S. Appl. No. 14/137,116.
International Preliminary Report on Patentability dated Aug. 20, 2015, issued to International Application No. PCT/US2013/043507.
Written Opinion of the International Searching Authority dated Dec. 22, 2014, issued to the corresponding International Application No. PCT/US2013/043507.
Written Opinion of the International Preliminary Examining Authority dated Dec. 31, 2014, issued to the corresponding International Application No. PCT/US2013/043507.
Chinese Office Action dated Sep. 28, 2016, issued to corresponding Chinese Application No. 201410291428.6.

* cited by examiner

SECTION B-B

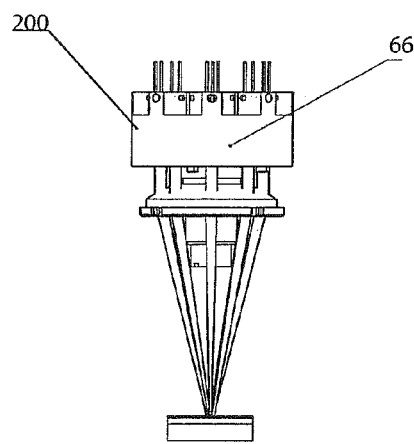
FIG 21
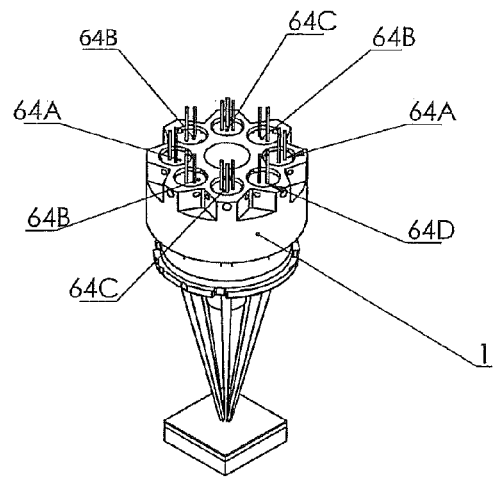
FIG 22
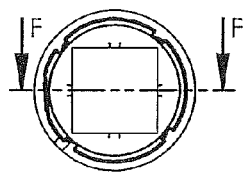
FIG 23
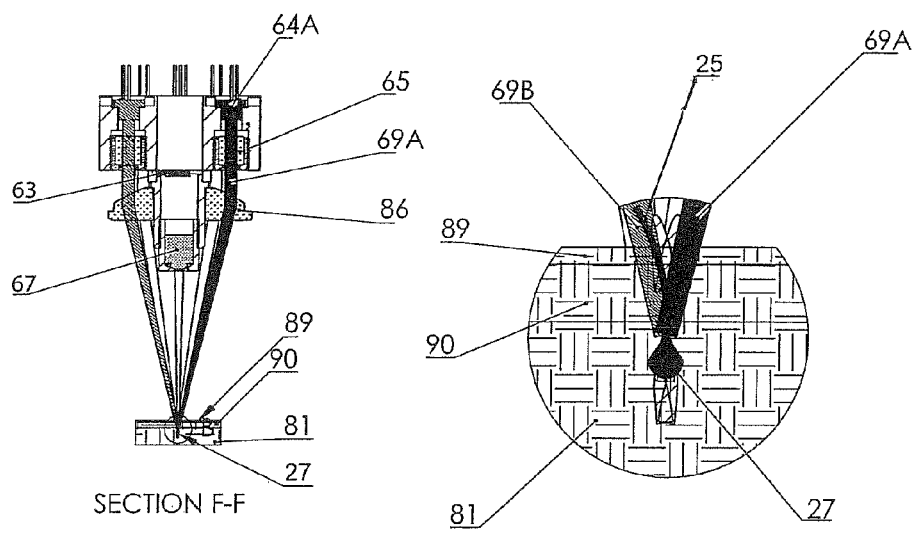
SECTION F-F
FIG 24
FIG 25

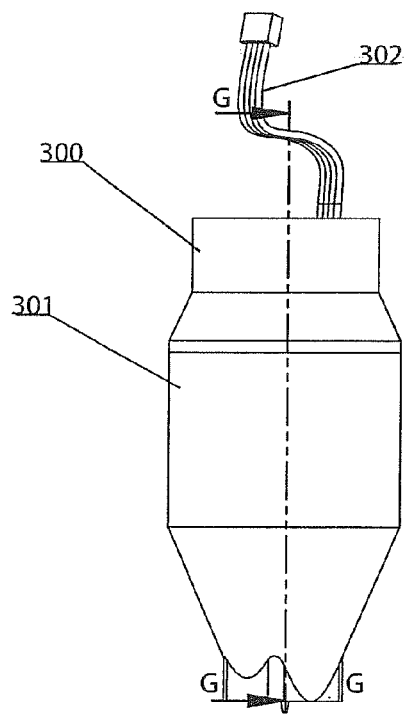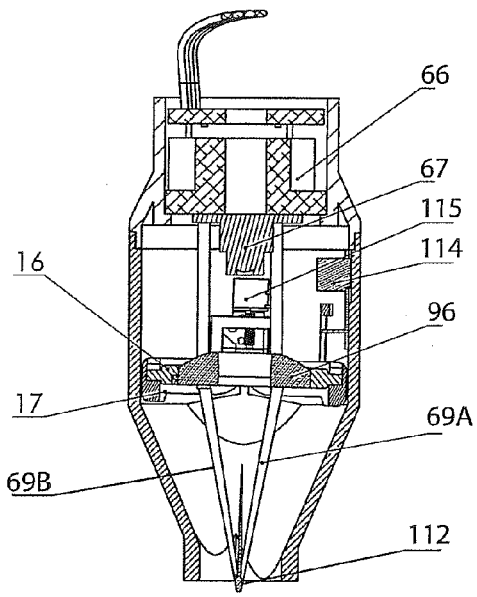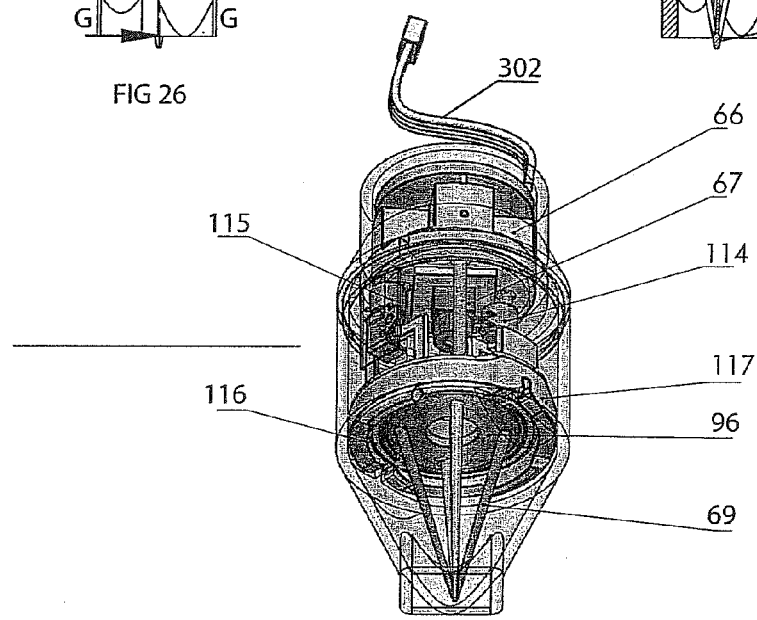
FIG 26
FIG 27
FIG 28

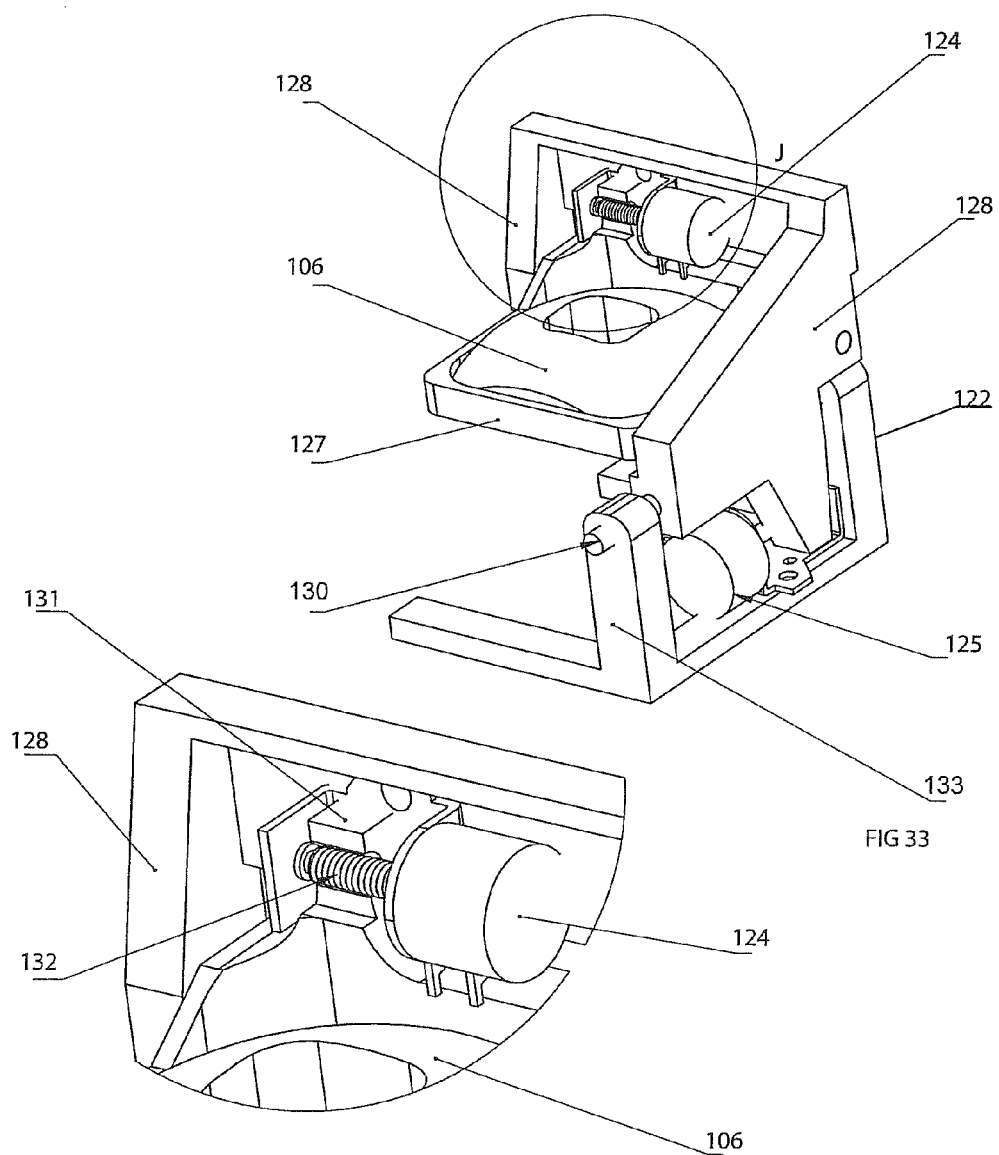

AESTHETIC TREATMENT DEVICE AND METHOD

CROSS-REFERENCE TO RELATED APPLICATIONS

This application is a divisional of U.S. application Ser. No. 14/137,116, filed Dec. 20, 2013, which is a continuation-in-part of U.S. application Ser. No. 13/903,129, filed on May 28, 2013, now pending, which claims the benefit of European Application No. 12173261.4, filed on Jun. 22, 2012, in the European Patent Office.

BACKGROUND OF THE INVENTION

1. Field of the Invention

Aspects of the invention relate to a miniature device which performs aesthetic treatments such as acne treatment, wrinkle removal, hair removal, rejuvenation and other applications based on light treatment. The system may comprise a detection system which evaluates the exact area to be treated and a multiple wavelength laser or LED sources tuned to optimally treat the unwanted aesthetic disorder and aimed at a single point or a plurality of points from different directions.

2. Description of the Related Art

In known aesthetic treatment devices, treatment is performed by flooding a relatively large area of skin with light without differentiation between healthy skin and the area to be treated. A typical system for dermatological treatment is described in US Patent Publication No. 2009/0054880 A1 intended to perform dermatological treatment by intense pulses of light radiated over large skin areas. The treatment selection is performed by chromatic characteristics of the skin or hair follicles and selection between treated and not to be treated areas is performed by the light source wavelength selection in a process called photo thermolysis or wavelength depended light absorption.

Light is absorbed by dark objects, so laser energy can be absorbed by dark material in the skin, but with higher speed and intensity. This dark target matter, or chromophore, can be naturally-occurring or artificially introduced. The main drawback of this procedure is that large areas of skin are unnecessarily exposed to high levels of intense pulsed light with potential adverse results.

For example, conventional laser hair removal systems rely on flooding large areas with high intensity light, hair removal is performed at wavelengths that will not damage the human tissue, such that the light will be transmitted by the skin to the follicle depth and destroy the follicle by photothermolysis.

SUMMARY OF THE INVENTION

Since small features on the skin surface are difficult to discern due to lack of contrast, especially when the colors of feature and skin surrounding are similar, a special peripheral illumination system is disclosed which greatly improves the contrast.

A specialized illumination technique that capitalizes on oblique illumination enhancing the image contrast is disclosed. This contrast enhancement technology is especially applicable in discerning small features with low contrast, such as blonde or white hair on top of pale skin. The illumination increases contrast by two mechanisms; oblique illumination (about 90 degrees to the optical axis of a camera) and multiple wavelength illumination from UV to infrared, each providing complementary color to a given feature. Light passing through a glass substrate will be reflected only from non-uniform features on the skin surface, illumination from oblique angles at all azimuths is diffracted, refracted, and reflected towards the camera objective to form a bright image of the specimen superimposed onto a primarily dark background.

A special imaging device with sensitivity matching the light sources will be used to detect and discern the areas to be treated from the surrounding areas. A second optional visible illumination light source will be used to illuminate the skin surface for positioning and image display. Selection of areas to be treated will be performed by spatial discernment rather than wavelength chromatic selection.

The treating source will comprise a laser or an LED with an appropriate wavelength dedicated to a specific treatment application. Preferably, the light source will be a dual wavelength laser capable of performing treatment by being transmitted through the skin or by local skin penetration. The system's laser power is sufficient to produce a beam capable of penetrating the epidermis and destroying a selected target. Penetration is achieved by selecting the right wavelength to be transmitted by the skin to the target area or alternatively by increasing power density to levels that will locally perforate the epidermis and destroy targets for example, hair follicles, color pigment stains and other skin disorders such as wrinkles. A special controllable power supply will allow operation of a treatment light source under a continuous or a pulse light mode. The laser beam used in laser rejuvenation and wrinkles removal will be targeted at the wrinkle outline. It simultaneously heats the underlying skin, called the dermis. This action works to stimulate growth of new collagen fibers. As the treated area heals, the new skin that forms is smoother and firmer. As for acne, a different wavelength source will be used, usually in the 400 nm region combined with a longer wavelength for heating the underlying skin.

Acne occurs when the body begins producing an overabundance of oils and sebaceous fluids that become trapped beneath the surface due to cuticle build up or debris. When this happens, unnatural levels of bacteria can begin to form, which can trigger infections.

Laser systems will be arranged to converge on a spot or spots from different directions, creating a powerful spot or spots of multi wavelength lasers on one hand and a highly diverging beam on the other hand, thereby improving the system safety. A special smart guiding mechanical system is provided for accurately selecting the area to be treated with micron accuracy.

One feature of uniqueness of the present aesthetic treatment device is that this device achieves and sometimes overcomes the performance of the systems existing in the market for the above procedures, while integrating all the capabilities of aesthetic treatment in a miniature hand held apparatus. The treatment apparatus is based on multiple light sources, lasers or LEDs focused on the treatment area from different directions. The multiple light sources for treatment purposes could have the same wavelength or different wavelengths each optimized for a different application. Target selection is performed by a dual wavelength smart illumination system. An internal light source structure enables the aesthetic treatment device to operate with high peak intensity for effective treatment, while the emission spectrum remains mostly in the near infra-red region. Aiming the multiple focused beams to target is performed manually or automatically.

Due to the above features, the proposed aesthetic treatment device is potentially usable for all hair types since its working principle is based on spatial hair removal rather than selective photothermolysis.

Another advantage of the proposed aesthetic treatment device is that the same provides an image display of the working area near and around the light sources, enabling treatment directly by a user even in concealed areas.

In addition, the high source focus ability and miniature size enables the use of a well designed miniature treatment hand piece.

Many disadvantages of prior art aesthetic treatment devices are advantageously solved by aspects of the present invention. A partial list is as follows:

In prior art systems a high power light or laser is applied to a relatively large area and the required treatment is usually achieved by photothermolysis followed by collateral damage to the surrounding skin. It is an aspect of the present invention to overcome this drawback by applying a focused laser beam or light directly to the treatment location without affecting the surrounding skin.

Some prior art treatments are performed by selective photothermolysis or by skin limited transparency to allow deep light penetration. It is another aspect of the present invention to perform treatment by spatial recognition of an area to be treated, enabling focused treatment and potential treatment, not only by photothermolysis but by a direct localized system.

In some prior art devices, the irradiated area is discernible only by visible illumination from above with poor image contrast in some cases, yet aspects of the present invention art provide an additional peripheral illumination which improves the contrast of features on the skin surface.

In some prior art devices, the light source is relatively large, requiring a large amount of power and complicated power electronics. It is another aspect of the present invention to provide a miniature treatment laser or LED with low power requirements, and which potentially is operated from a USB power source.

In some prior art devices, the light source is usually a single light source per treatment handle and in the case of a laser hand piece, the light radiates in a very limited light spectrum of a few nanometers. It is another aspect of the present invention to overcome these by using a dual wavelength miniature laser or mounting several lasers or an LED at the same treatment laser head for improved efficacy.

According to an aspect of the present invention, a miniature aesthetic treatment device discerns features to be treated on a skin surface by a peripheral illumination system based on multiple low power wavelength LED sources and is equipped with multiple high power wavelength light sources intended for therapeutic purposes directed to the features to be treated. The multiple high power wavelength light sources are preferable to a dual wavelength laser diode equipped with a focusing element. The multiple high power light sources are preferably mounted on a mechanical device serving as an optical bench and are aimed to have a point of intersection. A mechanical guidance system and an imaging device are provided to guide the focused laser energy to the treatment point on or under the skin surface.

There is provided in accordance with an embodiment of the present invention, an aesthetic treatment device comprising: a multi illumination system having at least one source in the visible region, disposed around a periphery of a predetermined area of skin; an imaging device, sensitive to the illumination system, to discern features on or under the skin within the predetermined area of skin to be treated; multiple treatment light sources mounted on an optical bench and aimed and focused to a point of treatment within the predetermined area of skin; a mechanical guidance system to guide the multiple treatment light sources; a pulse generator to control power output of the multiple treatment light sources based upon the treatment to be applied to the predetermined area of skin.

According to an embodiment, the multiple treatment light sources are of different wavelengths enabling different aesthetic procedures to be applied as the treatment.

According to an embodiment, the mechanical guidance system comprises a base having at least one spherical portion and a body which is manually operable about the at least one spherical portion, to manually operate the aesthetic treatment device in near spherical movements.

According to an embodiment, the mechanical guidance system comprises a motor to move the mechanical guidance system, and the aesthetic treatment device further comprises a dedicated computerized controller to control the motor.

According to an embodiment, the aesthetic treatment device further comprises a moving focusing optical system to create different beam sizes of the light sources based upon the treatment to be applied to the predetermined area of the skin treated by the treatment light sources.

According to an embodiment, the aesthetic treatment device further comprises a registration device to mark treated areas.

There is provided in accordance with another embodiment of the present invention, a method for a dermatological aesthetic treatment with a device comprising: illuminating a predetermined skin area using multiple light sources around a periphery of the predetermined skin area, the multiple light sources having at least one source in the visible region; discerning a feature on or in the predetermined area of the skin by generating an image of the feature illuminated by the multiple light sources; and controlling power output of treatment light sources to perform treatment on the feature.

According to an embodiment, the controlling of the power output of the treatment light sources comprises generating different wavelengths of light between the treatment light sources based upon the treatment to be performed.

According to an embodiment, the method further comprises moving the treatment light sources spherically about a base having at least one spherical portion.

According to an embodiment, the method further comprises moving the treatment light sources using a motor.

According to an embodiment, the controlling of the power output of the treatment light sources comprises generating different beam sizes between the treatment light sources.

According to an embodiment, the method further comprises marking the predetermined area of skin treated.

There is provided in accordance with an embodiment of the present invention, an aesthetic treatment device, comprising: an imaging device to generate an image of a predetermined area of skin; multiple treatment light sources provided in pairs, one of each pair have a same wavelength as the other in the pair and has a different wavelength from at least one other pair, wherein focused beams of the multiple treatment light sources are aimed and focused at the predetermined area of skin and to simultaneously perform a treatment on a feature of the predetermined area of skin according to the image generated; and a controller to adjust output of the multiple treatment light sources to vary the treatment based on the treatment to be performed.

There is provided in accordance with an embodiment of the present invention, an imaging device to generate an image of a predetermined area of skin; multiple treatment light sources provided in pairs, each pair having a same wavelength as the other in the pair and having a different wavelength from at least one other pair, wherein focused beams of the multiple treatment light sources are aimed and focused according to the wavelengths thereof at different focal points along a line at different depths under the skin according to the wavelengths thereof at the predetermined area of skin and to simultaneously perform a treatment on a feature of the predetermined area of skin according to the image generated; and a controller to adjust output of the multiple treatment light sources to vary the treatment based on the treatment to be performed.

There is provided in accordance with an embodiment of the present invention, an aesthetic treatment device, comprising: an imaging device to generate an image of a predetermined area of skin; multiple treatment light sources aimed and focused according to the image generated at a particular point within the predetermined area of skin; a focal point movement mechanism, to adjust a location of the particular point of focus within the predetermined area of skin; and a controller to adjust output of the multiple treatment light sources to vary the treatment based on the treatment to be performed.

There is provided in accordance with an embodiment of the present invention, a method for performing an aesthetic treatment on a predetermined area of skin, comprising: generating an image of the illuminated predetermined area of the skin; and generating outputs from pairs of multiple treatment light sources to simultaneously perform the treatment based upon the image of the predetermined area of the skin, wherein one of each pair has a same wavelength as the other in the pair, each pair having a different wavelength from at least one other pair.

There is provided in accordance with an embodiment of the present invention, a method for performing an aesthetic treatment on a predetermined area of skin, comprising: generating an image of the illuminated predetermined area of the skin; generating outputs from multiple treatment light sources to simultaneously perform the treatment based upon the image of the predetermined area of the skin; and focusing the outputs from the multiple outputs at different focal points according to wavelength along a line of depth into the skin.

Additional aspects and/or advantages of the invention will be set forth in part in the description which follows and, in part, will be obvious from the description, or may be learned by practice of the invention.

BRIEF DESCRIPTION OF DRAWINGS

These and/or other aspects and advantages of the invention will become apparent and more readily appreciated from the following description of the embodiments, taken in conjunction with the accompanying drawings of which:

FIG. 4 is cross-sectional view of the aesthetic treatment device shown in FIG. 1, revealing a bottom up view of the aesthetic treatment device, wherein FIG. 1 is a cross-sectional view along A-A;

FIG. 21 is a schematic representation of an aesthetic treatment device according to another embodiment of the present invention;

FIG. 22 is a peripheral view of a portion of the aesthetic treatment device shown in FIG. 21;

FIG. 23 is a top cross-sectional view of the aesthetic treatment device shown in FIG. 21;

FIG. 24 is a cross-sectional view of the aesthetic treatment device along line F-F of FIG. 23;

FIG. 25 is a cross-sectional view of a skin surface and under the skin portion of a person on whom the aesthetic treatment device shown in FIG. 21 is being used;

FIG. 26 is an exterior view of an aesthetic treatment device according to another embodiment of the present invention;

FIG. 27 is a cross-sectional view of the aesthetic treatment device shown in FIG. 26;

FIG. 28 is a perspective view of the aesthetic treatment device shown in FIG. 26;

FIG. 33 is a perspective view of a lens lateral movement mechanism that is used by an aesthetic treatment device instead of the tilt (dual axis angular movement) mechanism shown in FIGS. 27 through 32;

FIG. 34 is a blown up perspective view of the relationship between a motor and a frame to linearly move a lens used in the lens lateral movement mechanism shown in FIG. 33.

DETAILED DESCRIPTION OF EMBODIMENTS

Figure 1:
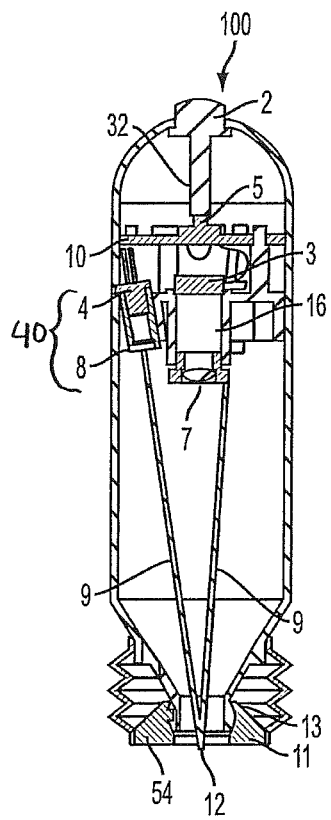
FIG. 1 is schematic representation of an aesthetic treatment device according to an embodiment of the present invention.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

Aspects of the present invention disclose an aesthetic treatment device enabling application of focused light beams directly to skin disorders, including miniature ones like hair follicles, stains, wrinkle lines, tattoo particles, miniature veins, etc., by treating the disorder with minimal or no effect on the surrounding skin.

Aspects of the present invention disclose an aesthetic treatment device enabling recognition of areas of skin to be treated. Recognition of the disorder is performed by a dual illumination system and the application of coherent or noncoherent multiple focused light sources directly to a specific recognized target for aesthetic treatments.

Aspects of the present invention disclose a dual illumination system, such that an additional illumination system is provided in addition to a "regular" illumination system. The so called regular illumination system illuminates the skin from above and it is mounted around a camera lens. The configuration usually results in good illumination for the skin, but due to back reflections, hair and hair roots are not easily seen. The additional illumination system is mounted on a peripheral area of a system opening as shown in the relevant drawing, and provides illumination which is parallel to the skin. Features protruding out from the skin will be strongly illuminated while the skin will remain in relative darkness, creating an improved image emphasizing hair and outer surface features.

Figure 2:
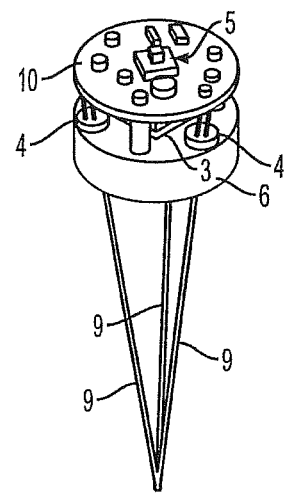
FIG. 2 is a blown up peripheral view of a portion of the aesthetic treatment device shown in FIG. 1.

FIG. 1 is a schematic representation of an aesthetic treatment device 100 according to an embodiment of the present invention. An imaging apparatus 16 includes a camera system 7 and a miniature imaging device 3 (see FIGS. 1 and 2). The camera system 7 is a multispectral camera system sensitive to the visible spectrum and infrared spectrum. The miniature imaging device 3, preferably, but not necessarily, a charge coupled device CCD, receives the images obtained by the camera system 7, and provides a visual of the images obtained by the camera system 7 for viewing by a user. The aesthetic treatment device 100 may be connected to a computer screen, a tablet or a cell phone, or a regular screen like a television screen, wirelessly or through a USB or other connection element, or connected to an analog screen via a connector cable or other connection element. An illumination system 11, in this instance, LEDs or miniature lamps, are disposed in the peripheral area of the skin of a person to be treated (either the user or another party). The immerging illumination is primarily parallel to the skin surface, thereby improving the contrast of different features on the skin surface. Treatment light sources, such as laser modules 40, each having a laser diode 4 and focusing optics 8, are mounted on a miniature optical bench 6, with each laser diode 4 having a focused beam 9 and aimed at the same aiming point 12 on or under the skin. Each laser diode 4 sits in a housing such that the housing sits inside the miniature optical bench 6, and the miniature optical bench 6 has the necessary electronics (e.g., an electronic chip) to drive the laser diode 4.

The LEDs 4 may have different wavelengths. The aesthetic treatment device 100 is equipped with a firing button 2 which is exposed and protrudes externally from the outer surface 1 of the aesthetic treatment device 100 (see FIG. 3), and a firing contact 5 connected to the firing bottom 2 by a connecting element 32. A pulse pattern of the LEDs 4 is either predetermined in advance, such as at the factory, or may be selected by a user via software which is accessible to the user. By pushing the firing bottom 2, the firing contact 5 moves to activate the laser modules 40, to produce the predetermined pulse pattern or pulse duration. A special spherical bearing 13 pivots and thus scans the focused beams 9 across the skin surface. The user, who is performing hair removal or rejuvenation by self-activating the aesthetic treatment device 100 or performing hair removal or rejuvenation on another person, moves the upper part of the aesthetic treatment device 100 (outer surface 1) around the spherical bearing 13 to provide a delicate laser movement at the skin surface. In FIG. 4, line A-A shows a cross-section of the aesthetic treatment device 100 (see FIG. 1 for cross-sectional view along A-A) where the concentric circles represent an elastic element sealing the spherical bearing 13. Moving the outer surface 1 manually around the spherical bearing 13 will steer the LEDs 4 to different locations. Scanning of the aiming point 12 is provided by manually moving the aesthetic treatment device 100 around such a pivot.

The treatment lasers or LEDs 4 are equipped with the focusing optics 8 to adjust beam size by moving up and down of the focused beams 9 which are directed towards the specific treatment skin area, then performing localized treatment without significant damage to the surrounding skin area. A registration device 54 is for registration purposes for the user to be able to mark and register the areas he/she has already treated.

An electronics board 10 includes a control unit and a pulse generator. The control unit controls beam parameters to be applied to the skin. Control is performed through the pulse generator and performs intensity duration as required for a particular aesthetic skin treatment. The pulse generator can be operated by the user pressing the firing button 2, the user can select the power by software loaded on a computing device or can have the power displayed on a TV screen, and some separate device to control the power.

Figure 5:
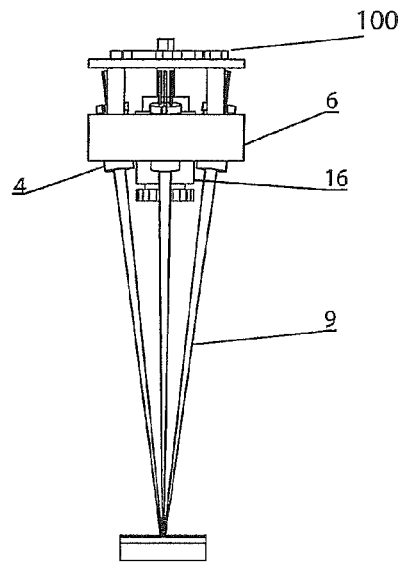
FIGS. 5-9 are schematic, perspective, cross-sectional and blown up views of the aesthetic treatment device shown in FIG. 1, wherein the aiming point of focused beams are under the surface of the skin and at a hair follicle.
Figure 6:
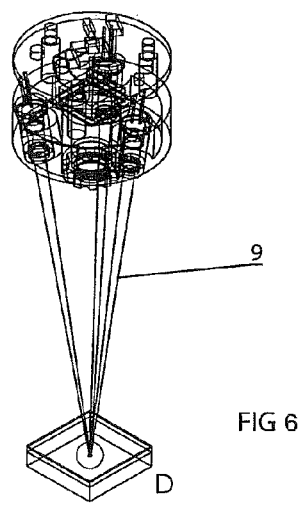
Figure 7:
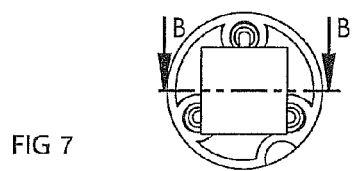
Figure 8:
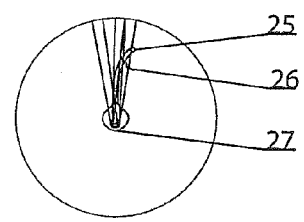
Figure 9:
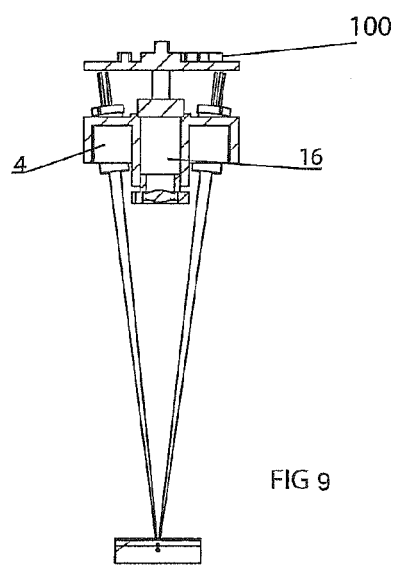

FIGS. 5-9 are schematic, perspective, cross-sectional and blown up views of the aesthetic treatment device 100 and the LEDs' 4 operation, such as FIGS. 5, 6 and 7, along with a blown up of the skin surface area (see FIG. 8) when the focused beam penetrates the skin epidermis, according to an embodiment of the present invention. The imaging apparatus 16 identifies hair 25, at a shaft 26 location and in some cases its follicle 27 location. The imaging apparatus 16, being multispectral sensitive to the infrared spectrum, will discern the under the skin follicle 27 location (see FIGS. 8 and 9 in particular). The hair follicle 27 may also be in the border between the dermis and under the skin. FIG. 9 is a cross-sectional view of the aesthetic treatment device taken along cross-section B-B shown in FIG. 7.

Treatment laser sources (LEDs) 4, in this example configuration, have a single aiming (focusing) point 12, such that the aiming point 12 is provided in such a way that is located beneath the epidermis level of the skin and directly targets the shown hair follicle 27 or in its immediate surroundings (see FIG. 8). Each focused beam 9 penetrates the epidermis from a different location. The focused beams 9, at the skin level, are not yet focused and thus do not damage the epidermis. But at the approximate location of the hair follicle 27, the three focused beams 9 coincide and each beam is focused. The end outcome is a device focusing at the sub skin level spotting the hair follicle 27 as shown in detail in FIG. 9.

It should be noted that if the illumination system 11 is a thicker one, then the aiming point 12 would be on the surface of the skin instead of under the surface of the skin.

Figure 10:
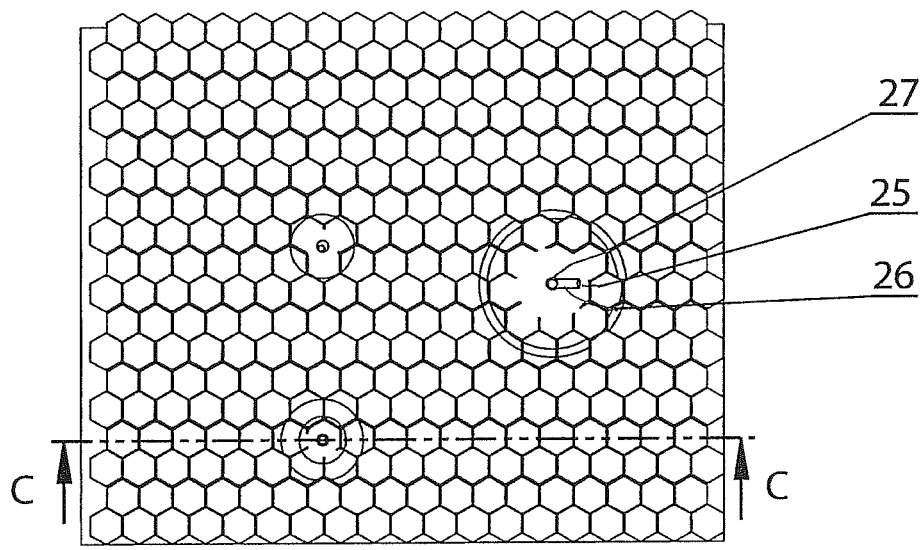
FIGS. 10 and 11 are a view of a predetermined area of skin imaged by a camera system of the aesthetic treatment device shown in FIG. 1 and a cross-sectional view of a skin surface and under the skin surface portion of a person on whom the aesthetic treatment device is being used.
Figure 11:
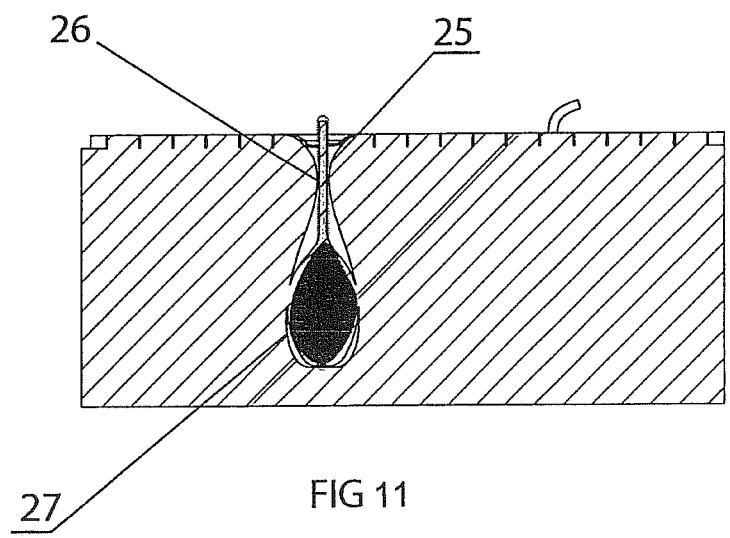

FIG. 10 show a portion of skin with skin areas having hairs 25, with the hair shaft 26 and the hair follicle 27 captured by the camera system 7 and as seen by the miniature imaging device 3 of the imaging device 16. FIG. 11 shows a cross-sectional view of the patient's body, including the skin surface and underneath the skin, taken along line C-C of FIG. 10. The skin is partially transparent to the camera system 7, the wavelengths of treatment of the focused beams 9 and the illumination system 11.

Figure 3:
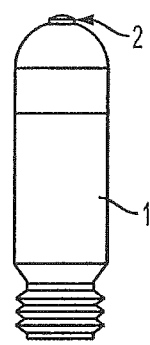
FIG. 3 is a view of the outer surface of the aesthetic treatment device shown in FIG. 1.
Figure 4:
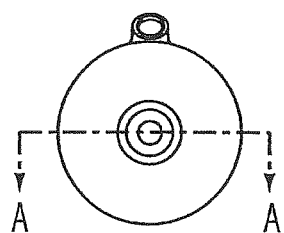

In FIGS. 1, 3 and 9, the camera system 7 takes the image of a portion of skin with skin areas having hairs 25 with hair shafts 26 and hair follicles 27. As noted, in this embodiment, the camera system 7 is stationary within the aesthetic treatment device 100, so that if a user wants to take an image of a different portion of skin, then the user needs to move the outer surface 1 of the aesthetic treatment device 100. The imaging apparatus 16 forms an image of the portion of the skin using the miniature imaging device 3, and provides that information to an external display such as a display panel, computer screen, tablet screen or any other type of screen.

The imaging apparatus 16 is able to see through the transparent surface of the skin, through to the hair follicle 27. The user is then able to move the aiming point 12 of the LEDs 4 to be at the position of hair follicle 27.

Figure 12:
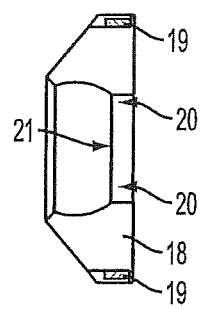
FIGS. 12-16 are blown up views showing an illumination system according to one embodiment of the aesthetic treatment device shown in FIG. 1.
Figure 13:
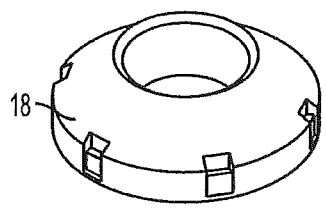
Figure 14:
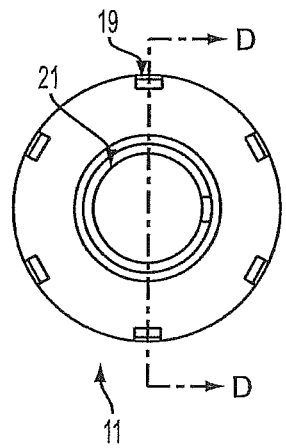
Figure 15:
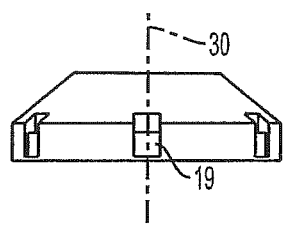
Figure 16:
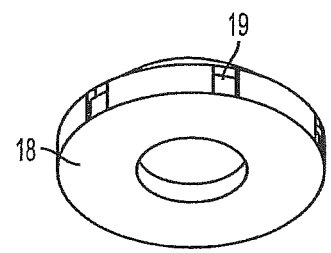

FIGS. 12-16 are blown up drawings of the illumination system 11 shown in FIG. 1. FIG. 12 reveals the basics of the illumination system 11. The proposed illumination system 11 includes a glass disk (substrate) 18 with illumination sources 19 at its perimeter. Illumination sources 19 output light of different wavelengths and can be controlled individually. The different wavelengths can provide for a better contrast between the skin surface and the area (skin features) to be treated. Light 20 travels in the glass disk substrate 18 almost perpendicular to a system optical axis 30, thus providing oblique illumination to the skin features to be observed. Here, the light output by the illumination sources 19 travels close to parallel to the skin. An inner aperture, of the glass disk substrate 18 can be a hollow 21 as shown in this configuration or solid. The illumination system 11 illuminates the area of the skin just underneath the circumference of the hollow (the area "within" the hollow) and the LEDs 4 treat the area of skin within the hollow to fix the aesthetic problem which is revealed therein. FIG. 12 is a view of the illumination system 11 along line D-D of the aesthetic treatment device 100 of FIG. 14, which is a bottom up view.

Figure 17:
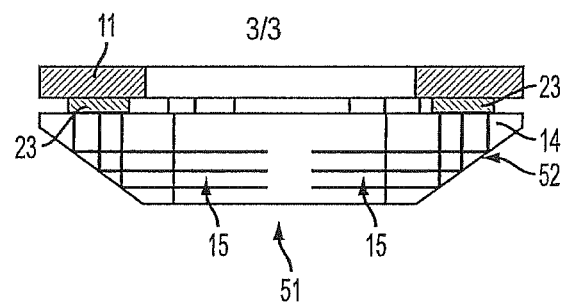
FIGS. 17-20 are blown up views showing an illumination system according to another embodiment of the aesthetic treatment device shown in FIG. 1.
Figure 18:
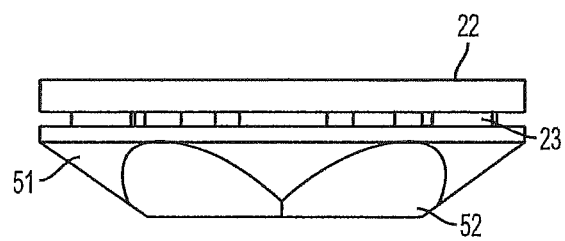
Figure 19:
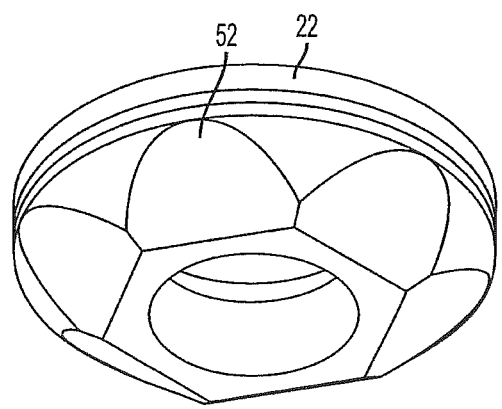
Figure 20:
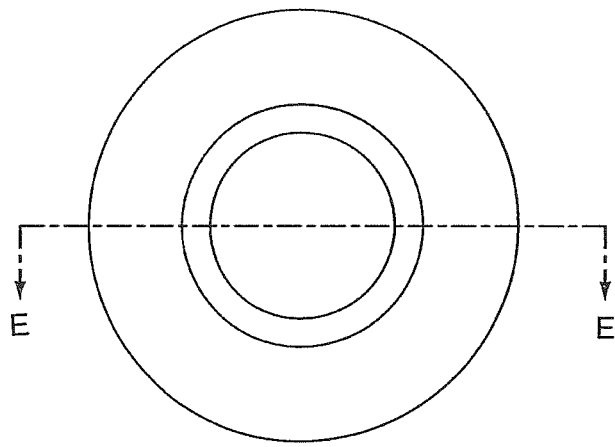
Figure 29:
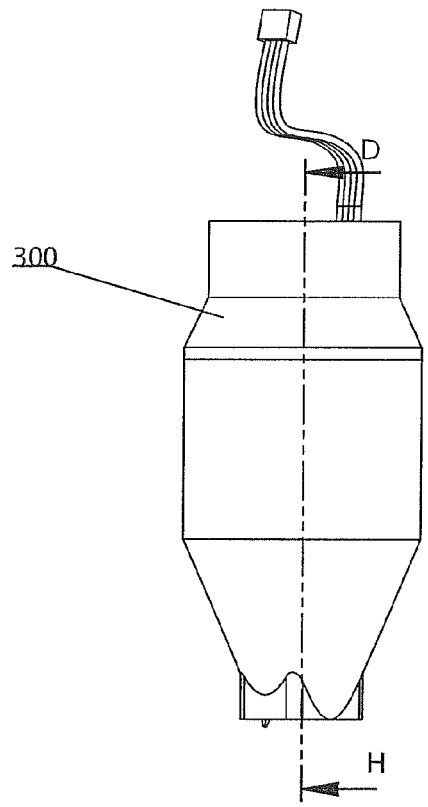
FIG. 29 is an exterior view of the aesthetic treatment device shown in FIG. 26 when the aiming point of treatment light beams is moved away from an original aiming point.

FIGS. 17-20 show a blown up section of an illumination system 51 according to another embodiment where illumination sources 23 are mounted on a printed circuit board 22 illuminating a transparent part 14 having reflective surfaces 52. The reflective surfaces 52 reflect light by 90 degrees, causing a light beam 15 to emerge almost parallel to the skin surface from the opening in the reflective surfaces 52. Thus unlike in FIGS. 12-16 where the illumination sources 19 are mounted on a periphery of a glass disk substrate 18 and light is emitted nearly parallel to the skin, in FIGS. 17-20, the illumination sources 23 direct light perpendicular to the skin and the reflective surfaces bend the light 90 degrees so as to be parallel to the skin. FIG. 17 is a cross-sectional view of the illumination system 5 (along E-E of FIG. 20), where FIG. 20 is a bottom up view of the illumination system 11 of the aesthetic treatment device 100.

FIGS. 21-25 show an aesthetic treatment device 200 according to another embodiment of the present invention. In this embodiment, multiple pairs of light sources (laser diodes) 64A, 64B, 64C and 64D are preferably mounted on an optical bench 66 and are aimed in the same direction so as to be parallel to each other and directly downward in the drawing. The optical bench 66 is similar to the optical bench 6 of the previous embodiments, with the necessary electronics (e.g., an electronic chip) to drive the laser diodes 64A-64D. The laser diodes 64A-64D are aimed at an under the skin area 11 in this embodiment (below the epidermis 89 and dermis 90), but can just as easily be aimed on a surface of the skin (epidermis 89). The laser diodes 64A-64D are paired, each pair is denoted by a same letter combination, i.e. 64A, 64B, 64C, or 64D, for a total of 4 pairs mounted as shown in FIGS. 21 and 22. There may be less or more than 4 pairs of laser diodes. Cross-section F-F in FIG. 23 of the aesthetic treatment device 200 is shown in FIG. 24. Each laser diode has a collimating lens 65 which collimates the light beam emitted therefrom. Each laser diode 64A-64D emits a corresponding laser light beam 69A-69D straight downward, but which is re-directed by a lens 86 to be focused toward an aiming point or aiming points along an optical axis of the lens 86. The lens 86 focuses the laser light beams 69A-69D below the skin in this instance, but could be in a configuration such that the laser light beams 69A-69D are focused on the skin surface instead.

A camera system 67, which has an imaging device 63 (which is a charge coupled device in this embodiment), magnifies an area of the skin and schematically shows the epidermis 89, the dermis 90 and the under the skin area 81. The hair follicle 27 is shown in FIGS. 24 and 25, at which the laser light beams 69A-69D are aimed. Each pair of light beams has a different wavelength and is focused by the lens at a different point underneath the skin 11 and along the system optical axis, creating multiple foci along the optical axis (see FIG. 25). This is due to the lens 86 bending the light by different amounts depending upon the wavelengths of the light beams passing therethrough. Generally, the higher the wavelength, the further is the aiming point from the aesthetic treatment device 200, and thus deeper into the skin. By having the pairs of light beams at different aiming points along an axis and deeper or shallower into the skin, there is an increased chance of removing the hair follicle since the user may not be able to determine the exact depth of the hair follicle 27.

The multiple pairs of light sources could be configured so that each pair emits light beams of the same wavelength but different from the other pairs as just described, but could also emit light beams all of the same wavelength. Further, the light beams could be paired in different frequencies of pulses and could be in the visible range, the infrared (IR) range or near ultraviolet (UV) range, depending upon the application/treatment to be performed by the aesthetic treatment device 200.

The lens could be a singlet, but could also have multiple lenses, such as two lenses, where the lens system can correct for wavelength so that all wavelengths are at the same focal point.

Based on the received image from the camera system 67, a user can aim the light beams 69A-69D to the target, such as a hair 25 and/or its follicle 27, in this specific application. The aesthetic treatment device 200 may incorporate the special spherical bearing 13 shown in the aesthetic treatment device 100 of FIG. 1 to enable the user to direct the aiming point 12 laterally, but has been left out to avoid redundancy and for ease of understanding.

The lens 86 has a hollow in the center, allowing for the camera system 67 to get a clear view of the skin portion underneath the aesthetic treatment device 200.

The illumination system 11 may be incorporated into this embodiment in a similar fashion as was shown and described with reference to the aesthetic treatment device 100, but has been left out so to avoid redundancy and for ease of understanding.

FIGS. 26-32 show an aesthetic treatment device 300 according to yet another embodiment, one that incorporates the capability to move the laser focusing point across an imaged skin portion without moving an outer surface 301. In this embodiment, the configuration of the laser diodes 64A-64D and optical bench 66 from the previous embodiment and a lens 96 (which can be the same as the lens 86 or lens system used in the previous embodiment) are used. This capability is achieved by tilting the lens 96 in two axes. FIG. 26 shows the external view of the aesthetic treatment device 300 with an outer surface 201 and connection cables 302 for connecting the aesthetic treatment device to a display and/or computing device. The connection cables 302 are also usable for the previous embodiments. It is also conceivable for any of these embodiments that the communication with the display and/or computing device can take place wirelessly, as well as through a wired connection.

Figure 30:
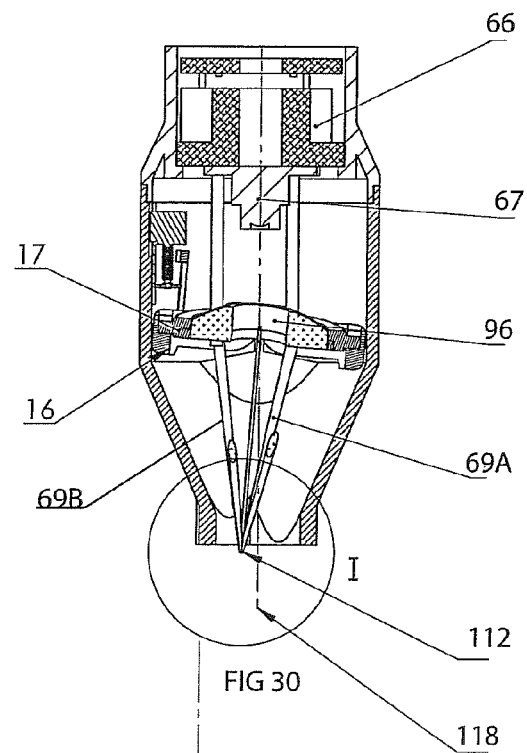
FIG. 30 is a cross-sectional view of the aesthetic treatment device shown in FIG. 26 when the aiming point of treatment light beams is moved away from an original aiming point.

FIG. 27 shows a cross-sectional view of the lens system (or singular lens) 96 along cross-section G-G of FIG. 26 when the lens 96 is in an original untilted position. FIG. 28 is a schematic view of the aesthetic treatment device 300. FIG. 30 shows a cross-section view of the lens system (or singular lens) 96 along cross-section H-H of FIG. 29 when the lens 106 is tilted relative to the original untilted position. This lens 96 concentrates the multiple laser light beams 69A-69D emitted by corresponding laser diodes 64A-64D mounted on the optical bench 66 to an aiming point or points 112 along the optical axis of the lens 96. Motors 114 and 115 will tilt two orthogonal oriented frames 116 and 117 about axes 120 and 121, respectively, thereby transmitting the tilt motion to the lens element 96. For relatively small tilting motion, even when the camera system 67 shows a skin area with the outer surface 301 of the aesthetic treatment device 300 in a particular position on the body of someone to which the treatment is being applied, the motion of the frames 116 and 117 about orthogonal corresponding axes 120 and 121, causes rotation of the lens 96, and this effect will scan the laser focused beams 69A-69D across the skin area, without any additional movement of the outer surface 301 of the aesthetic treatment device 300. The movement amount is proportional to the lens 96 tilt. In this instance, the frames 116 and 117 act as gimbals. The lens 96 may tilt 3 or 4 degrees according to an aspect of the present invention.

Figure 31:
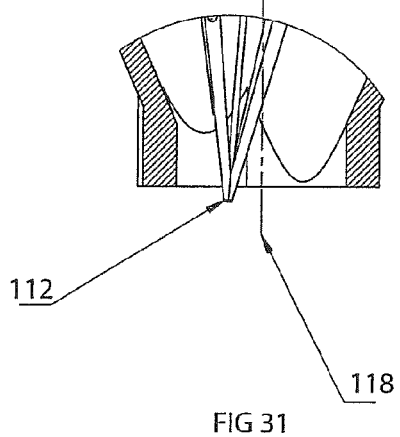
FIG. 31 is a blown up view showing the aiming point of the treatment light beams of the aesthetic treatment device shown in FIG. 26, wherein the aiming point is moved away from the original aiming point.
Figure 32:
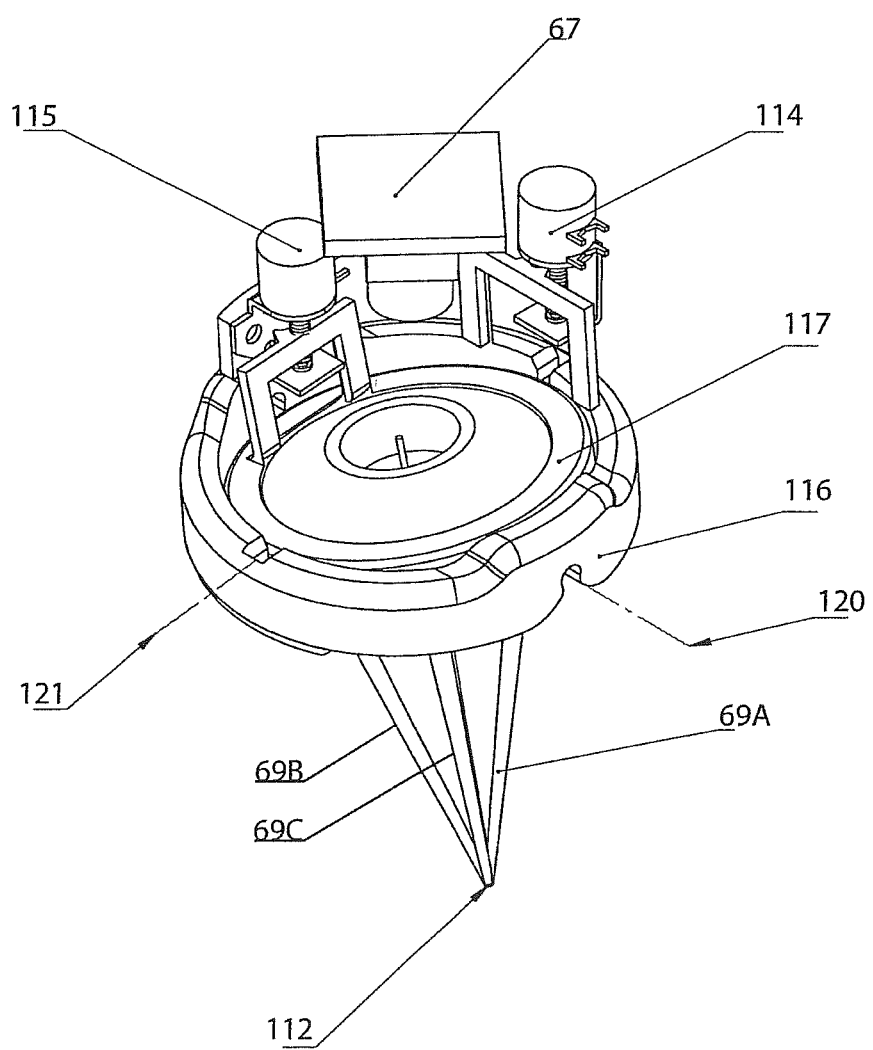
FIG. 32 is peripheral view showing a tilt mechanism to tilt a lens for focusing light beams of the aesthetic treatment device of FIG. 26.

FIG. 31 is a magnification of a tilted position of the aiming point 112 when the frames 116 and 117, and thus the lens 96, are tilted relative to the original laser beam position (optical axis) 118 when the lens 96 was untilted. FIG. 32 shows in detail the tilting mechanism with the motors 114 and 115 and the two orthogonal axes 120 and 121, which are pivot axes for frames 116 and 117. The frame 117 here is glued to the lens 96. The aiming points 112 are moved away from the original optical axis of the lens 96 corresponding to when the lens 96 is in an original starting position.

The lens 96 has a hollow in the center, allowing for the camera system 67 to get a clear view of the skin portion underneath the aesthetic treatment device 300.

In this embodiment, the user can adjust the lens position to treat various skin features, like hairs 25, by aiming the light beams 69A-69D at the hair follicle 27 or hair follicles 27 under the skin that are within view of the camera system 67, without moving the outer surface 301 of the aesthetic treatment device 300. Alternatively, a computing system (not shown), upon receiving the image of a skin portion, can run an algorithm to determine the location or locations of hair follicles within the skin portion for which the image is generated, and then aim the light beams 69A-69D at desired locations of each of the hair follicles within that skin portion by powering the motors 114 and 115 to rotate the lens 106 through the frames 116 and 117. In that way, a user simply has to place the aesthetic treatment device 300 over a skin portion, and without doing anything else, the aesthetic treatment device can eliminate each hair follicle (and thus hair) that is located within that skin portion, thereby easing use by the user. The user may even be able to see the fumes from the hair follicles getting zapped. By pinpointing the locations of the hair follicles, and zapping only the specific locations, less damage and pain are caused to the skin, as opposed to the related art, which zaps a general skin portion without finding the exact location of the hair, nor focusing on the hair follicle under the skin.

Under this embodiment, since the aiming point(s) 112 can be moved laterally through the rotation of the lens 96, the special spherical bearing 13 as shown in FIG. 1 is not necessary.

The illumination system 11 may be incorporated into this embodiment in a similar fashion as was shown and described with reference to the aesthetic treatment device 100, but has been left out so to avoid redundancy and for ease of understanding.

FIG. 33 is a perspective view of a lens lateral movement mechanism 122 that replaces the dual axis angular movement mechanism shown in FIGS. 26 through 32, and its function is to scan the laser beams 69A-69D laterally across the predetermined area of the skin. The lateral movement is performed parallel to the skin and the ratio of lens 106 movement to laser movement across the skin is unity. The lens 106 is optically identical to previous scanning lenses, such as lens 96, but with a different mechanical outline. A frame 127 holds the lens 106 and is attached to a nut element 131 (see FIG. 34) and is moved linearly by a motor 124 along an axis 129 (see FIG. 35). A mechanical frame 128 holds the motor 124, and is attached to another nut (not shown). A linear mechanism is shown by the magnified section J of FIG. 33 in FIG. 34, where a screw like shaft 132 of the motor 124, engaged with the nut element 131, moves the nut element 131 so that the frame 127 moves along the axis 129 relative to the mechanical frame 128. A frame 133 holds another motor 125 with a screw like shaft (not shown) to engage a nut element (not shown) attached to the mechanical frame 128. Thus in a similar way, the motor 125 moves the mechanical frame 128 along orthogonal axis 130, to move the lens 106 in a direction orthogonal to the axis 129. The frame 133 is attached to an outer housing of the anesthetic device 400. The aiming points 112 are moved away from the original optical axis of the lens 106 when the lens 106 is in an original starting position, similar to the movement (but due to different operation from that of the lens 96) of the aiming points shown in FIGS. 30 and 31.

Figure 35:
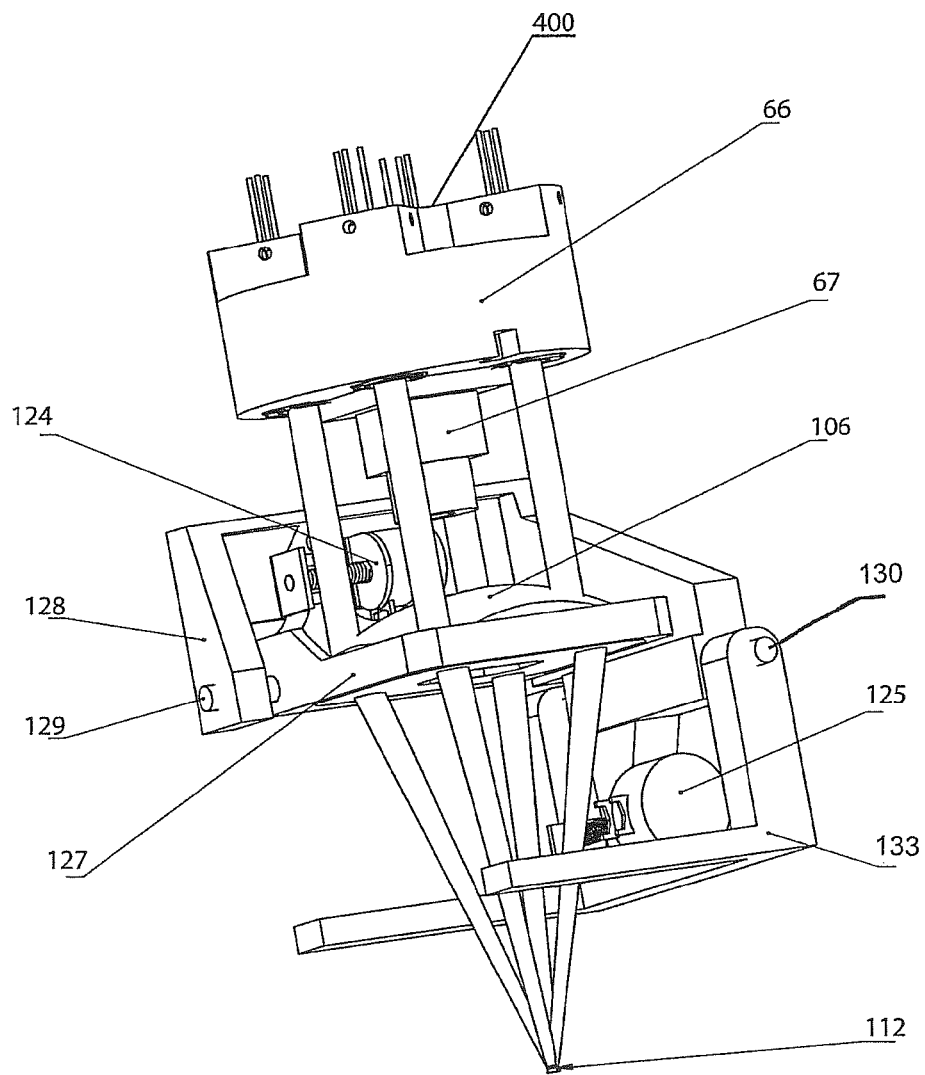
FIG. 35 shows a perspective view of the aesthetic treatment device using the lens lateral movement mechanism shown in FIG. 33.

FIG. 35 shows the same lens lateral movement mechanism 122 shown in FIGS. 33 and 34, with some added features that are present in previous embodiments, like the optical bench 66, the camera system 67 and the laser aiming point or points 112, thereby illustrating an aesthetic treatment device 400 according to another embodiment of the present invention.

In this embodiment, the user can adjust the lens 106 position to treat various skin features, like hairs 25, by aiming the light beams 69A-69D at the hair follicle 27 or hair follicles 27 under the skin that are within view of the camera system 67, without moving an outer surface (not shown) of the aesthetic treatment device 400. Alternatively, a computing system (not shown), upon receiving the image of a skin portion, can run an algorithm to determine the location or locations of hair follicles within the skin portion for which the image is generated, and then aim the light beams 69A-69D at desired locations of each of the hair follicles within that skin portion by powering the motors 124 and 125 to laterally move the lens 106 through the movement of the frame 127 and mechanical frame 128. In that way, a user simply has to place the aesthetic treatment device 400 over a skin portion, and without doing anything else, the aesthetic treatment device 400 can eliminate each hair follicle (and thus hair) that is located within that skin portion, thereby easing use by the user. The user may even be able to see the fumes from the hair follicles 27 getting zapped. By pinpointing the locations of the hair follicles 27, and zapping only the specific locations, less damage and pain are caused to the skin, as opposed to the related art, which zaps a general skin portion without finding the exact location of the hair, nor focusing on the hair follicle under the skin.

Under this embodiment, since the aiming point(s) 112 can be moved laterally through the rotation of the lens 96, the special spherical bearing 13 as shown in FIG. 1 is not necessary.

The illumination system 11 may be incorporated into this embodiment in a similar fashion as was shown and described with reference to the aesthetic treatment device 100, but has been left out so to avoid redundancy and for ease of understanding.

Accordingly, a device and method of an aesthetic treatment device is disclosed. The device includes multiple focused beams to be selectively aimed at the area of the skin to be treated. Aspects of the present invention relate to a method for aesthetic treatment where multi wavelength light sources combined with an adequate imaging device is used to select the target skin area and an appropriate laser light combination is used to treat the skin area target. The treatment is performed by aiming focused light sources or laser beams on or under the skin which are powerful enough to penetrate and destroy hair follicles which are in between the skin and under the skin or under the skin, treat acne and treat other dermatological disorders on or under the skin. More specifically, aspects of the present invention relate to a miniature aesthetic treatment device capable of performing non-contact treatment to a limited area of the skin of a person, to treating dermatological disorders such as hair follicles, acne glands, tattoo removal, wrinkles, age stains, rejuvenation and other superficial dermatological treatments. The imaging device is capable of recognizing the area to be treated and may use an effective illumination device, such as the illumination system, illuminating the area of the skin to be treated from its periphery, thereby improving the contrast between the skin and skin surface disorders.

Known methods use a relatively large light source with a specific wavelength range, which floods a large skin area, the light source being capable of selective treatment by photothermolysis. For example, hair removal is based on the principle of selectively heating and destroying the hair follicle while avoiding significant damage to surrounding skin or tissue. Hair follicles are selected by photothermolysis, which is a method based on the fact that hair absorbs greater amounts of light, due to its darker color when compared with surrounding skin tissue, and a similar mechanism will work for other treatments such as skin stains and miniature over exposed veins. Hair is thus automatically selected by the light since it has a darker color and thus higher absorption coefficient. On the other hand, hair or other skin disorders brighter than the surrounding skin area are difficult if not impossible to treat by prior art techniques. It is a purpose of the aesthetic treatment device according to an embodiment of the present invention to offer a different method based on spatial selection of hair follicles or other targets, destroying the follicle by focused light energy with little to no damage or exposure to surrounding skin or tissue.

One of the main limitations of existing methods is the usage of the photothermolysis effect which relies on color difference between normal skin and the area to be treated, where a basic requirement is for the skin to be significantly brighter than the hair follicle or glands or and basically transparent to the used wavelength. That is the main reason that light colored (such as blonde) and white hair are almost impossible to treat using existing devices and methods since they are brighter than the surrounding skin. It is a purpose of this invention to offer a solution free of those prior art limitations.

Aspects of this invention relate generally to an aesthetic treatment device and method to detect the position of a small area of skin to be treated and focus a light source on the specific area (on or under the skin) without affecting, and damaging the surrounding skin area.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A method for performing a dermatological treatment on a predetermined area of skin, comprising:
   placing an illumination system having an aperture on the predetermined area of the skin;
   exposing the predetermined area of skin through the aperture;
   illuminating the predetermined area of skin with the illumination system which has the aperture by emitting, from multiple illumination light sources disposed around a periphery of the aperture, multiple illumination beams having different wavelengths in the UV to infrared region in free space across the aperture over the predetermined area of skin and in a parallel direction to the skin surface;
   generating an image of the illuminated predetermined area of the skin with an imaging device by imaging the illuminated predetermined area of the skin through the aperture and through a central hole of a hollow focusing lens; and
   generating laser beams from multiple treatment laser sources having different wavelengths, the multiple treatment laser sources arranged on a circumference of an optical bench in pairs by same wavelength, wherein the illumination system, the laser sources, the optical bench and the hollow lens are housed together in a handpiece;
   adjusting a power output of the laser beams based on the dermatological treatment to be applied to the predetermined area of skin;
   propagating the laser beams through the aperture of the illumination system, focusing the laser beams under the skin with the hollow focusing lens, moving a focal point of the laser beams by tilting the hollow lens relative to the aperture of the illumination system, and performing the dermatological treatment with the propagated multiple treatment light sources based on the generated image.

2. The method according to claim 1, the method further comprising bending and focusing the laser beams according to wavelength and penetrating the surface of the skin at multiple different locations, wherein each pair of focused laser beams has a focal point along a focal axis at a different depth under the skin from each other pair of focused laser beams.

3. The method according to claim 2, wherein the focal points of the laser beams are under the surface of the skin.

4. The method according to claim 2, wherein the propagating of the laser beams comprises directing the laser beams parallel to one another towards a lens, and bending and aiming the parallel laser beams at the focal points under the skin.

5. The method according to claim 4, wherein the propagating of the laser beams comprises using the lens which is a circular lens to bend and aim the parallel beams at the focal points under the skin.

6. The method according to claim 4, wherein the aiming points of the laser beams are each along an optical axis of the lens, but at a different distance from other pairs of focused beams from the lens.

7. The method according to claim 5, wherein the aiming points of the laser beams are each along an optical axis of the lens, but at a different distance from other pairs of focused beams from the lens.

8. The method according to claim 4, wherein the lens is a circular lens with an the central hole to provide a free line of sight for the imaging device to the predetermined area of skin.

9. The method according to claim 2, wherein the illumination system has the aperture along an optical axis, and the imaging device is along the optical axis.

\* \* \* \* \*